United States Patent [19]
Saffer et al.

[11] Patent Number: 5,436,461
[45] Date of Patent: Jul. 25, 1995

[54] MEDICAL APPARATUS HAVING A C-ARM AND A CABLE GUIDE

[75] Inventors: Edmund Saffer, Eggolsheim; Helmut Richter, Baiersdorf; Adelbert Kupfer, Poxdorf; Josef Zettl, Buckenhof, all of Germany

[73] Assignee: Siemens Aktiengesellschaft, Munich, Germany

[21] Appl. No.: 239,119

[22] Filed: May 6, 1994

[30] Foreign Application Priority Data

Jun. 14, 1993 [DE] Germany ............. 43 19 598.9

[51] Int. Cl.⁶ ............................................. H05G 1/02
[52] U.S. Cl. ............................ 250/522.1; 378/194; 378/197
[58] Field of Search .............. 250/522.1; 378/193, 378/194, 196, 197, 198

[56] References Cited

U.S. PATENT DOCUMENTS 4,866,752 9/1989 Bock et al. .................. 378/197
4,961,214 10/1990 Van Endschot et al. ..... 378/197

FOREIGN PATENT DOCUMENTS

3406221A1 8/1985 Germany.
4111780 10/1992 Germany.

OTHER PUBLICATIONS

Siemens Brochure for Siremobil 2000-1/2000-2, Dec. 1992.

Primary Examiner—Paul M. Dzierzynski
Assistant Examiner—Kiet T. Nguyen
Attorney, Agent, or Firm—Hill, Steadman & Simpson

[57] ABSTRACT

A medical apparatus has a C-arm which carries a radiation transmitter, and which is adjustably held by a mount so as to be movable along the circumference of the C-arm. The mount engages guideways which are provided at a rear side of the C-arm. The C-arm is in the form of a hollow, profiled part having a substantially U-shaped cross-section. The guideways are respectively disposed at the insides of the legs of the U-shaped cross-section. The C-arm has an interior channel therein with a rectangular cross-section, which is adapted for accepting electrical leads or supply lines for the radiation transmitter. The channel is laterally adjacent one leg of the U-shaped cross-section.

5 Claims, 3 Drawing Sheets

MEDICAL APPARATUS HAVING A C-ARM AND A CABLE GUIDE

BACKGROUND OF THE INVENTION

1. Field of the Invention

The present invention is directed to a medical apparatus of the type having a C-arm on which a component, such as a radiation transmitter, is mounted, with the C-arm being adjustable along its circumference by means of a mount which holds the C-arm.

2. Description of the Prior Art

A medical apparatus having a C-arm of the type described above which supports a radiation transmitter is commercially available from Siemens AG, designated SIREMOBIL 2000. The C-arm is adjustable along its circumference by means of guideways which are provided at a rear of the C-arm, and which engage the mount which holds the C-arm. The leads for the radiation transmitter, as well as for a radiation receiver, are internally guided in the C-arm. The leads are guided in a recess in the interior of the C-arm, as described in German OS 3406221.

SUMMARY OF THE INVENTION

It is an object of the present invention to provide a medical apparatus of the type described above having a C-arm which is adjustable along its circumference by means of a mount which holds the C-arm, which can be manufactured in an economic manner, which has a compact structure, and which provides covered means for guiding the leads to the component or components carried by the C-arm.

The above object is achieved in accordance with the principles of the present invention in a medical apparatus having a C-arm which is held in a mount and which is adjustable along its circumference, the C-arm carrying a radiation transmitter. The mount engages guideways disposed at a rear side of the C-arm, and the C-arm is in the form of a hollow, profiled part having a region exhibiting a substantially U-shaped cross-section. The guideways are respectively provided at the insides of the legs of the U-shaped cross-section. The profiled part forming the C-arm further includes an interior channel having a rectangular cross-section which is adapted to accept leads or supply lines for the radiation transmitter. The interior channel is disposed laterally adjacent one leg of the U-shaped cross-section.

An advantage of the medical apparatus having a C-arm constructed as described above is that the C-arm can be economically manufactured as a profiled part, and has low weight. As a result of the mount engaging guideways disposed at the insides of the legs of the U-shaped cross-section, the C-arm and the mount form a compact structure. By providing the profiled part with the interior channel having a rectangular cross-section that is laterally adjacent one leg, the leads for the radiation transmitter are guided in a covered manner, and moreover the assembly of the leads is simplified by providing free access to the rectangular channel. This also facilitates the replacement of leads.

DESCRIPTION OF THE PREFERRED EMBODIMENTS

Figure 1:
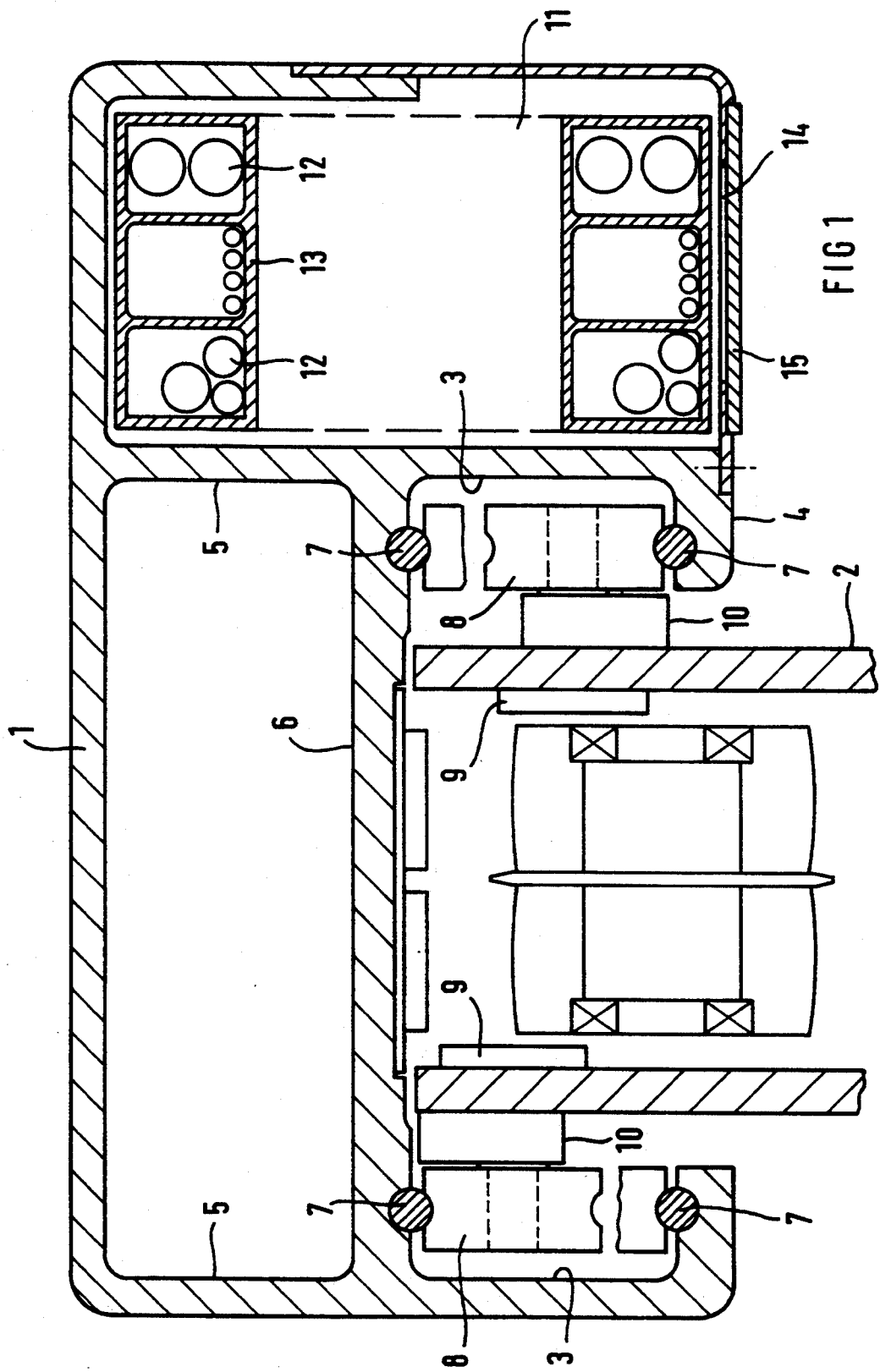
FIG. 1 shows a section taken through a C-arm of a medical apparatus constructed in accordance with the principles of the present invention.
Figure 2:
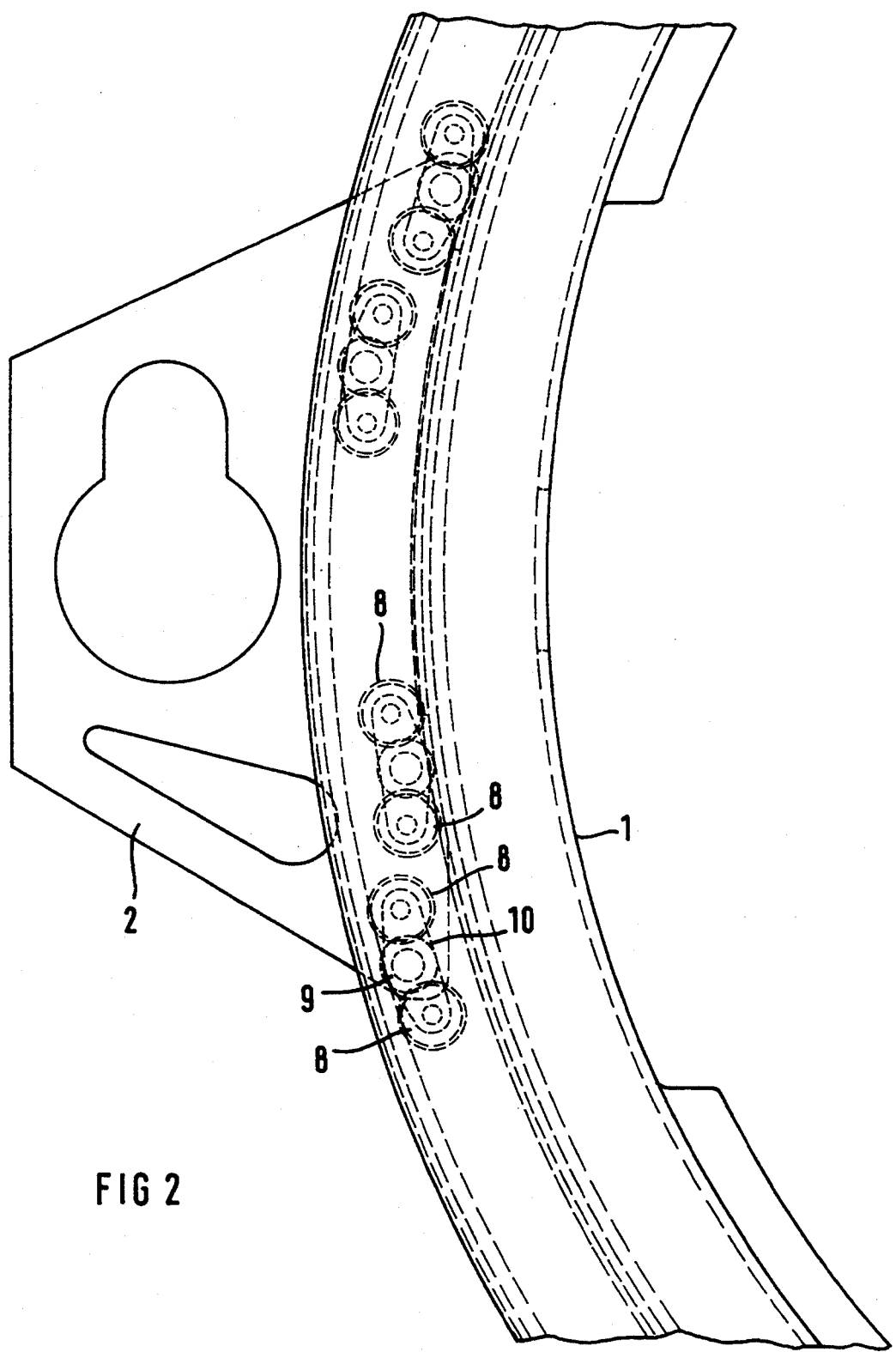
FIG. 2 is a side elevational view of a portion of a C-arm and its mount, constructed in accordance with the principles of the present invention.

FIG. 1 shows a C-arm 1 for a medical apparatus, constructed in accordance with the principles of the present invention, which is adjustably carried along its circumference by a mount 2. The C-arm 1 is fashioned as a hollow, profiled part, and has a region exhibiting a substantially U-shaped cross-section, with guideways 3 being respectively disposed at a rear side 4 of the C-arm 1 and at the insides of the respective legs 5 of the U-shaped cross-section. In a preferred embodiment, the legs are connected to each other by a web 6, the web 6 forming a wall of the hollow, profiled part. Guide wires 7, which are entrained around pulleys 8 of the mount 2, are disposed at the guideways 3 along the circumference of the C-arm 1, and opposite each other. As shown in FIG. 2, the pulleys 8 are adjustable, preferably by means of an eccentric element 9, so that a connection which is substantially free of play is achieved between the mount 2 and the guide wires 7 of the C-arm 1. A particularly precise guidance is achieved in an embodiment wherein the mount 2 is provided with a plurality of assemblies on each side of the C-arm 1, each assembly including a mount 10 carrying two pulleys 8 and the eccentric element 9.

Preferably the free ends of the legs 5 are angled so as to extend slightly into the opening of the U-shaped cross-section, and first guide wires 7 are disposed at the insides of the respective angled ends. Second guide wires 7 are seated at the web 6 disposed opposite the first guide wires 7. As a result, the mount 2 can extend into the U-shaped cross-section of the profiled part, thereby resulting in a space-saving structure.

Figure 3:
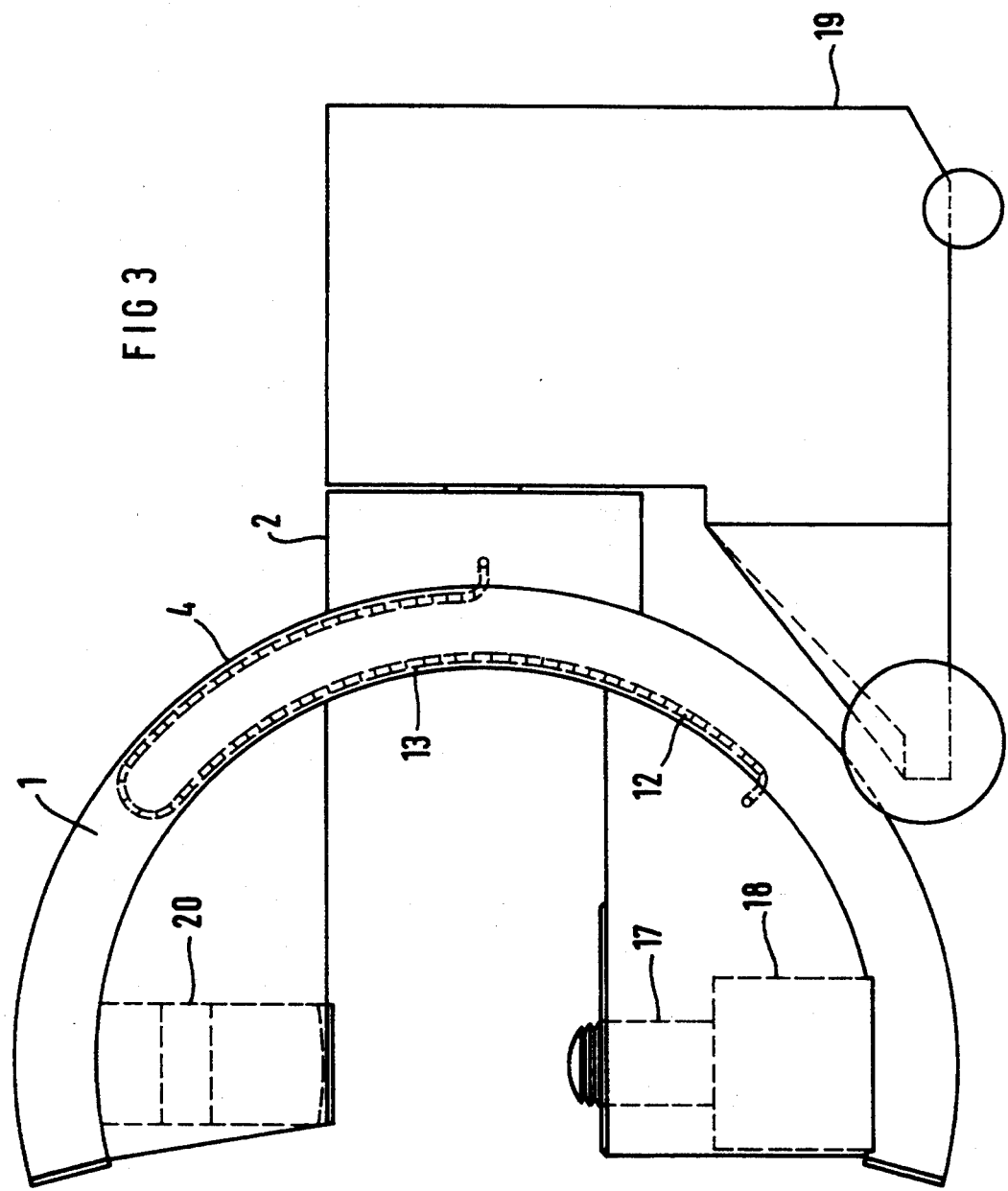
FIG. 3 shows an exemplary embodiment, in schematic form, of a medical apparatus having a C-arm and a mount with the cable guided in a preferred manner, constructed in accordance with the principles of the present invention.

The hollow profiled part forming the C-arm 1 includes a further region 11, in the form of an interior channel having a rectangular cross-section for accepting leads or supply lines 12 for a radiation transmitter. The further region 11 laterally adjoins a leg 5, preferably at the exterior thereof. For protection against damage and for improved guidance, the leads 12 are preferably contained within the region 11 in a guide chain 13 which, as shown in FIG. 3, is composed of a plurality of individual chain elements. This permits the leads 12 to be protectively guided in an arc.

At its rear side 4, the rectangular region 11 has an opening 14, through which the guide chain 3 with the leads 12 therein can be introduced or removed in a simple manner. In order to satisfy hygienic requirements, the opening 14 can be closed with a tape band 15 as a cover.

The C-arm 1 can carry a radiation transmitter which may be a source of acoustic waves 17 or an x-ray source 18, or both, as shown in FIG. 3. If the medical apparatus is an x-ray diagnostics apparatus, the C-arm 1 and its mount 2 can be held by a carriage 19, so as to be mobile, or can be arranged in a known manner employing a floor mount or a ceiling mount. If the apparatus is an x-ray diagnostics apparatus, the C-arm 1 can carry an image intensifier 20 at its end opposite the end at which the x-ray source 18 is disposed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical apparatus comprising:

a C-arm for carrying a medical component, said C-arm being formed by a hollow, profiled part having a circumference and a region having a substantially U-shaped cross section, said U-shaped cross-section having respective legs at opposite sides thereof and said U-shaped cross-section opening toward a rear of said C-arm;

guideways respectively disposed at said legs of said U-shaped cross-section facing toward said opening of said U-shaped cross-section;

mounting means for adjusting said C-arm along said circumference at said rear of said C-arm and engaging said guideways; and said hollow, profiled part forming said C-arm having a further region with a rectangular cross-section adapted for receiving electrical lines for said medical component, said further region disposed laterally adjacent one leg of said U-shaped cross-section.

2. A medical apparatus as claimed in claim 1 further comprising pulleys attached to said mount and guide wires extending along said legs of said U-shaped cross-section of said C-arm engaging said pulleys for adjusting said C-arm along said circumference.

3. A medical apparatus as claimed in claim 1 further comprising a guide chain in which said lines for said medical component are disposed, said guide chain being disposed in said further region.

4. A medical apparatus as claimed in claim 1 wherein said U-shaped cross-section is formed by a web connecting said legs, said web forming a wall of said hollow, profiled part.

5. A medical apparatus as claimed in claim 4 further comprising pulleys disposed on said mount and first and second guide wires attached to said C-arm and engaging said pulleys for adjusting said C-arm along said circumference, and wherein each of said legs has a free end which is angled toward said opening of said U-shaped cross-section, said first guide wires being respectively disposed at said angled free ends facing toward said opening of said U-shaped cross-section, and said second guide wires being disposed at said web, opposite said first guide wires, and facing toward said opening of said U-shaped cross-section.

* * * * *